United States Patent [19]
Heckele

[11] Patent Number: 5,476,473
[45] Date of Patent: Dec. 19, 1995

[54] INSTRUMENT FOR SURGICALLY CUTTING TISSUE

[75] Inventor: Helmut Heckele, Knittlingen, Germany

[73] Assignee: Richard Wolf GmbH, Knittlingen, Germany

[21] Appl. No.: 177,835

[22] Filed: Jan. 5, 1994

[30] Foreign Application Priority Data

Jan. 5, 1993 [DE] Germany .................. 43 00 064.9

[51] Int. Cl.$^6$ ............................ A61B 10/00; A61B 17/32
[52] U.S. Cl. ............................................. 606/171; 604/22
[58] Field of Search ......................... 606/170, 171; 128/151, 153, 154; 604/22

[56] References Cited

U.S. PATENT DOCUMENTS

| | | | |
|---|---|---|---|
| Re. 33,258 | 7/1990 | Onik et al. .................. | 606/171 X |
| 3,902,498 | 9/1975 | Niederer .................... | 128/305 |
| 4,340,046 | 7/1982 | Cox .......................... | 128/207 |
| 4,603,694 | 8/1986 | Wheeler ..................... | 606/171 |
| 4,644,951 | 2/1987 | Bays ......................... | 606/171X |
| 4,646,738 | 3/1987 | Trott . | |
| 4,674,502 | 6/1987 | Imonti ....................... | 128/751 X |
| 5,106,364 | 4/1992 | Hayafuji et al. ............ | 606/171 X |
| 5,285,795 | 2/1994 | Ryan et al. ................. | 606/171 X |
| 5,346,503 | 9/1994 | Chow ......................... | 606/170 |

FOREIGN PATENT DOCUMENTS

| | | |
|---|---|---|
| 0150245 | 8/1985 | European Pat. Off. . |
| 0347170 | 12/1989 | European Pat. Off. . |
| 0445918 | 9/1991 | European Pat. Off. . |
| 0530595 | 3/1993 | European Pat. Off. . |
| 1019048 | 11/1957 | Germany . |
| 7817220 | 9/1978 | Germany . |
| 8712835 U | 1/1988 | Germany . |
| 3630203 | 3/1988 | Germany . |
| 3716764 | 12/1988 | Germany . |
| 3828478 | 5/1989 | Germany . |

*Primary Examiner*—Stephen C. Pellegrino
*Assistant Examiner*—Nancy Mulcare
*Attorney, Agent, or Firm*—Panitch Schwarze Jacobs & Nadel

[57] ABSTRACT

A tissue punch for surgically cutting tissue is provided with an inner shaft having an opening with a cutting edge at its distal end, which collaborates with a counter cutting edge at the distal end of an outer shaft, so that during operation of the tissue punch tissue, which extends through the opening into the inner shaft, is separated by the two cutting edges moving against each other. The inner shaft is rigid and is straight in its proximal region but changes distally into a curved shape. The outer shaft, which moves axially on the inner shaft, is flexible at least in the area of the curve of the inner shaft.

10 Claims, 3 Drawing Sheets

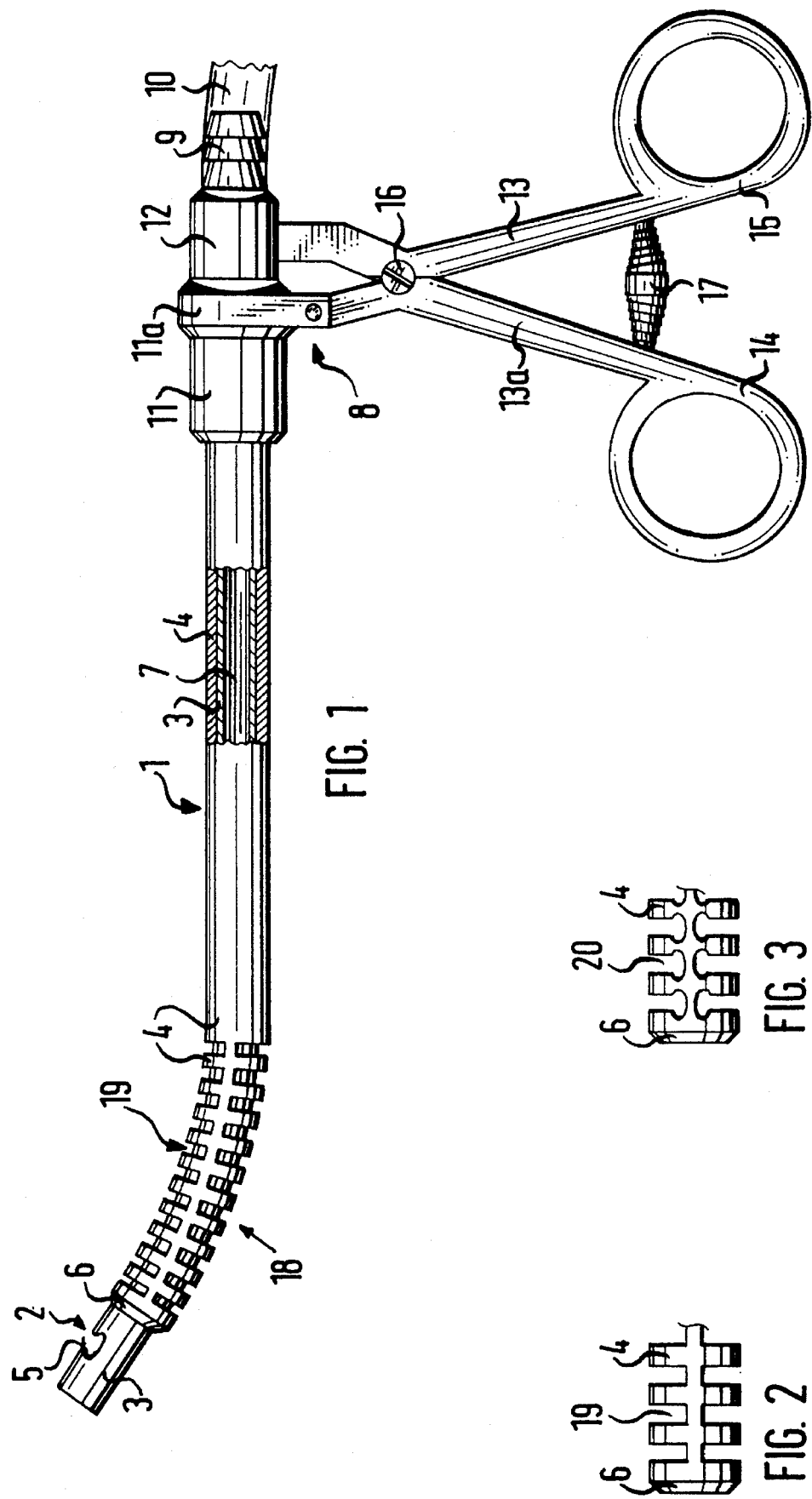

INSTRUMENT FOR SURGICALLY CUTTING TISSUE

FIELD OF THE INVENTION

The present invention relates to a surgical cutting instrument, particularly a tissue punch, which has an outer shaft and an inner shaft having an opening with a cutting edge at its distal end. The cutting edge collaborates with a counter cutting edge at the distal end of the outer shaft, so that upon actuation of the tissue punch tissue, which reaches through the said opening into the inner shaft, is separated by the two cutting edges moving against each other.

BACKGROUND OF THE INVENTION

Such a tissue punch is known, for example, from DE-GM 7 817 220. This instrument is equipped with a receiving part, in which the separated tissue particles are caught and which can be screwed off the instrument for emptying.

DE-PS 3 630 203 shows a surgical tissue punch, which is equipped with a suction apparatus for removal of the separated tissue pieces. This instrument essentially comprises an outer tube and an inner tube axially movable therein. The inner tube is provided at its distal end with a laterally opening hollow chamber, bordered by a cutting edge facing the outer tube. The cutting edge is applied to the tissue to be treated by having tissue pieces reach into the hollow chamber. By movement of the inner tube, by means of a corresponding actuation device, against the outer tube, which has a counter cutting edge corresponding to the cutting edge of the inner tube, the tissue pieces extending into the hollow chamber can then be cut. With the suction apparatus the tissue pieces can be sucked through the inner tube and out of the operation area. Suction occurs by applying a vacuum impulse to the inner tube when the two above-mentioned cutting edges touch or overlap each other. The separated tissue piece moves in this manner from the instrument to the collecting basin.

The above-cited tissue punches are constructed as straight, rigid instruments and are therefore poorly or not at all suited for many operations, for example in the thorax, since it is often necessary to carry out operations in areas which are difficult to reach.

This is possible with a flexible instrument shaft according to DE-AS 1 019 048 for surgical instruments, which can also be used in connection with tissue punches. This instrument shaft essentially comprises a spring wire helix with a slide guide slipping thereinto and is equipped at its distal end with a connection piece for the connection of different operating mechanisms. The wire helix surrounds a thin-walled and flexible tube, which stiffens the wire helix. In this way the entire instrument shaft is flexible and can be brought into the needed shape prior to usage.

However, using this instrument shaft as a carrier of a tissue punch mechanism it is necessary to extract the instrument shaft with the punching mechanism from the operation area for removal of the separated tissue pieces.

There are also tissue punches according to EP-OS 0 445 918 and U.S. Pat. No. 4,646,738 where the outer shaft is rigid and extends from a proximal straight region to a distal curved region, while the inner shaft is flexible so that it can conform to the outer shaft at its curved region. The motorized rotating inner shaft can be axially adjusted in the outer shaft and with a cutting edge at its end can be brought in contact with the tissue to be separated. The tissue extends through an opening of the outer shaft into its inner area, and the separated tissue is siphoned off through the inner shaft.

Apart from the fact that longitudinal movements of cutting parts are generally more effective than rotational movements due to a longer "open phase," such cutting instruments have some further disadvantages. The means necessary to make the inner shaft flexible, for example material cutouts, give rise to an irregular surface of the shaft canal with the consequence that the separated tissue cannot be sucked hindrance-free and with low friction through the inner shaft. In addition, problems develop with the cleaning and hygienic treatment of the instrumentation. Furthermore, an eventual breakage of the inner shaft cannot be visually noticed, and it also creates problems to remove a distal fragment of the inner shaft from the outer shaft. Finally, the operator cannot observe the instantaneous position of the cutting tool due to its covered location.

SUMMARY OF THE INVENTION

The invention involves a tissue punch which is free of such disadvantages. In particular, the cutting instrument should guarantee complete and problem-free suctioning of the separated tissue and give the operator the possibility of examining the position and function of the cutting edges, as well as the treatment result, for example through an endoscope.

For achieving these objects the foregoing tissue punch is constructed according to the invention in such a way that the inner shaft is rigid, runs straight in the proximal area and changes distally to a curved path, and that the outer shaft is deformable at least in this area of the curve.

The inner shaft is constructed as a tube which has a canal with a smooth, low friction surface, through which tissue can be easily siphoned off and which can be easily cleaned. Damage that might occur to the relatively heavily stressed outer shaft by frequent bending changes will be readily apparent to the naked eye. Since the cutting edges are freely visible from the outside, the operator has the further possibility of continuously optically viewing the treatment location, as well as the location and functioning of the cutting edges, such as through use of an endoscope in a separate tube.

In one embodiment, the laterally directed opening of the inner shaft can have a proximally directed cutting edge, while a ring-shaped counter cutting edge is formed from the distal end of the outer shaft.

The counter cutting edge, working together with the cutting edge of the inner shaft, can also be constructed on an elastically deformable cutting part, which is provided at the distal end of the outer shaft and can be moved on a curved course, which is determined by guides and the distal form of the inner shaft. Such an embodiment ensures the possibility that the related opening of the inner shaft can be arranged not only toward the side, but also directed distally. The cutting edges on both shafts can also be formed from edges of holes, which can be brought into alignment.

In order to achieve an easy deformability of the outer shaft, it is provided with recesses, which lie opposed to one another on the radiuses of the curve of the inner shaft.

The inner shaft has a free lumen, which connects with its environment through its opening. Proximally the inner shaft is connected with a connection nozzle such that the inner bore which forms the free lumen of the inner shaft aligns with the inner bore of the connection nozzle, so that a vacuum apparatus connectable to the connection nozzle can siphon off the separated tissue without problems and without complications.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings, like numerals are used to indicate like elements throughout.

FIG. 1 is a side view of a tissue punch of the invention, partially displayed in cross-section;

FIG. 2 is an embodiment of the distal end of the outer shaft;

FIG. 3 is a further embodiment of the distal end of the outer shaft;

DETAILED DESCRIPTION OF PREFERRED EMBODIMENTS

Figure 4:
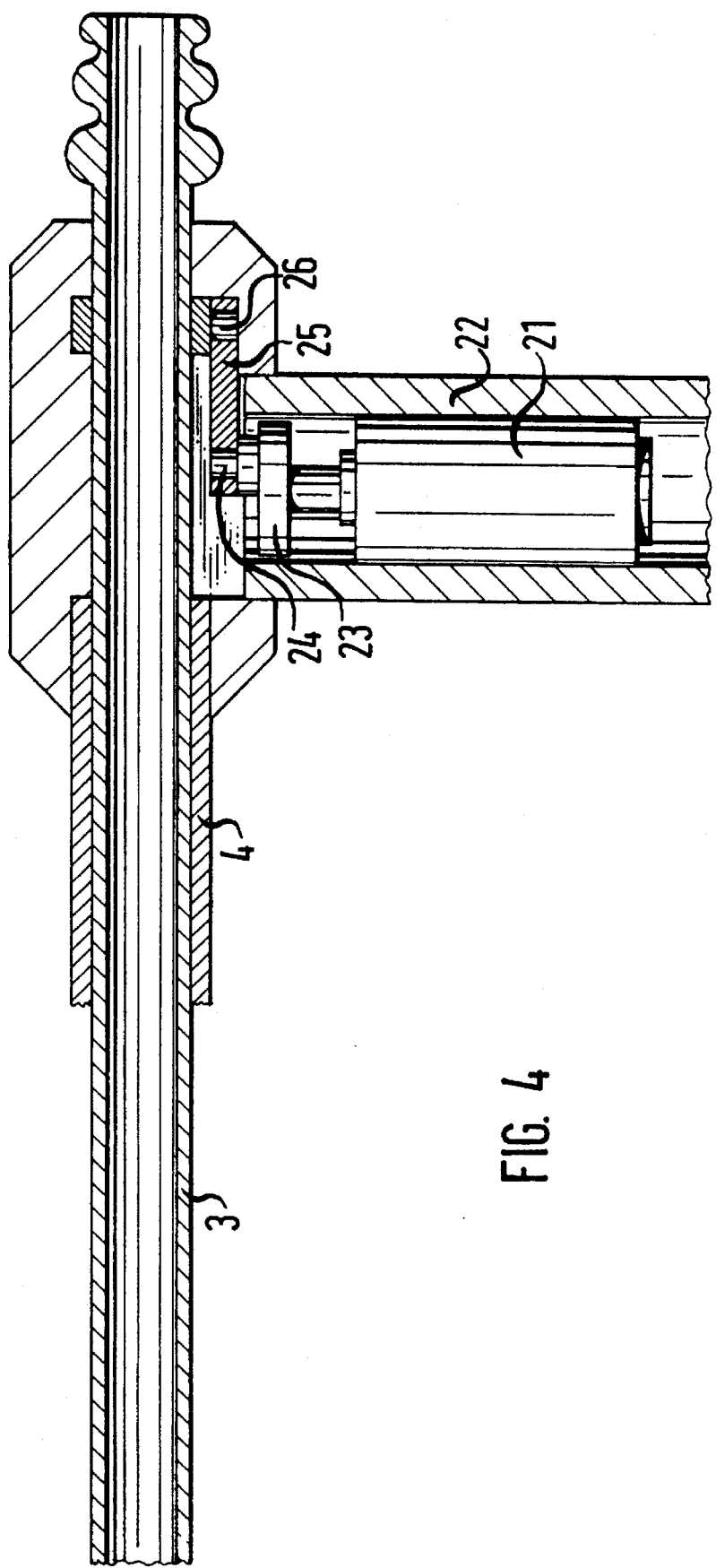
FIG. 4 is a cross-sectional side view of a motor-activated tissue punch according to the invention.

The tissue punch according to FIG. 1 comprises an inner shaft 3 with a lateral opening 2 at its distal end, on which an outer shaft 4 is axially movable. The opening 2 has a cutting edge 5, which during the punching or cutting process operates together with a cutting edge 6 on the distal end of the of the outer shaft 4. The cutting edge 6 is formed by the sharp end of the outer shaft 4. The inner shaft 3 has a free lumen in connection with the opening 2, and is provided proximally with a connection nozzle 9 onto which a suction hose 10 can be connected. The arrangement of the connection nozzle 9 is such that its inner bore aligns with the free lumen of inner shaft 3, so that a suction canal is thereby formed extending from the lateral opening 2 to the proximal end of the instrument. The suction hose leads to a suction apparatus (not shown).

The hand piece 8 comprises a shell 11, which is connected on the one side with the outer shaft 4 and on the other side through a reinforcing part 11a with a scissor leg 13a of the hand piece. Proximally to the shell 11 the inner shaft 3 and the connection nozzle 9 are fastened to a second shell 12, which is connected with a second scissor leg 13. The two scissor legs 13 and 13a terminate in scissor grips 14 and 15 and are pivotably connected to one another by a screw 16. A pressure spring 17, shaped as a two-sided volute spring, holds the scissor legs 13 and 13a apart, so that the opening 2 of the inner shaft 3 extends completely out of the distal end of outer shaft 4 of the tissue punch. In this position, the shell 11 with its reinforcing part 11a lies against the distal end of the shell 12, which has a greater diameter than the shell 11, and therefore serves as a limit stop for the reinforcing part 11a of the shell 11.

The tissue punch 1 has a curved region 18 in its distal section. The curve arises from the correspondingly curved inner shaft 3, on which the outer shaft 4 is supported. The outer shaft can conform to the curve of the inner shaft 3 by having opposing recesses 19 in the form of radial cuts, which merely leave a narrow material bridge in between. The flexibility of this bendable region 18 of the outer shaft 4 can be established by the number, arrangement and geometry of the recesses 19.

FIG. 2 displays a first embodiment of this bending area, wherein the recesses 19 are made by simple sawing or milling cuts with angular profile.

FIG. 3 displays a further embodiment in which the recesses 20 have at their ends a shape, which is indeed expensive to manufacture, but can endure very tight bends. The number of achievable bending changes with this embodiment is higher than with the embodiment in FIG. 2, since this embodiment is free of stress concentration.

For cutting of tissue or tissue pieces the tissue punch, is laid against the tissue to be removed, so that pieces thereof extend into the opening 2 of the inner shaft 3. By actuation of the scissor grips 13 and 13a against the pressure spring 17, the outer shaft 4 with its cutting edge 6 is pushed toward the opening 2 until the cutting edge 5 of the opening 2 and the cutting edge 6 of the outer shaft shear, so that the tissue piece to be removed is separated. The tissue piece thus falls into the free lumen 7 in the inner shaft 3 and can be sucked out of the inner shaft 3 through the vacuum hose 10 into the vacuum apparatus.

The inner shaft 3 and also the outer shaft 4 are preferably made of metal, so that the cutting edges 5 and 6, can be formed directly on these parts. However, it is also possible for the outer shaft 4 to be made of plastic, whereby the cutting edge 6 can then be formed by a separate insert of metal.

FIG. 4 shows in a simplified embodiment a motorized tissue punch with an electric motor 21 in a housing 22, which forms a hand grip to hold the tissue punch. A peg 24, which fits into a bore of a connecting rod 25, sits eccentric to the rotation axis on a disc 23, which is rotatably driven by the motor. A driving pin 26, which is attached to the inner shaft 3, extends into a further bore of this rod.

The inner shaft 3 is set into oscillating movements, relative to the stationary or fixed outer shaft 4 by the so formed eccentric drive of the running motor 21; whereby in corresponding manner to the hand actuation as previously described in connection with FIG. 1, the cutting edges of the tissue punch are moved for separation of the tissue.

Figure 7:
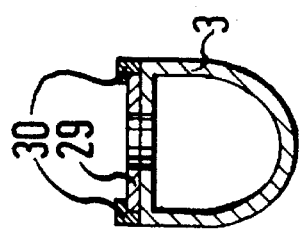
FIG. 7 is a cross section along line VII—VII in FIG. 5.
Figure 5:
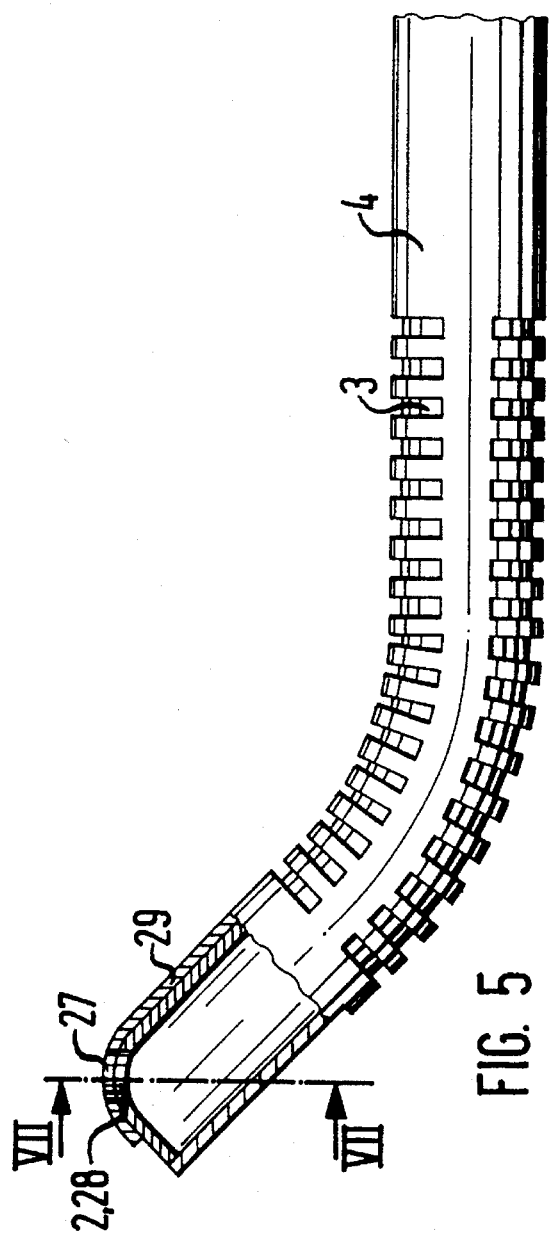
FIG. 5 is the distal end of a tissue punch in side view with a special form and arrangement of the cutting edges.
Figure 6:
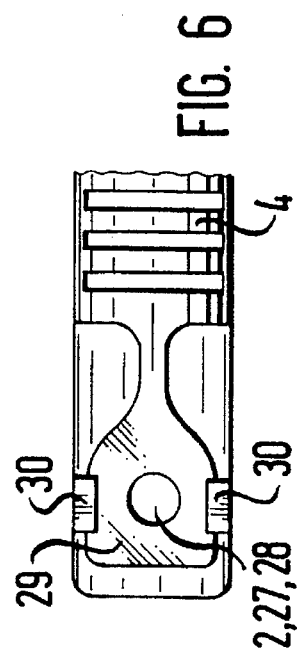
FIG. 6 is a top view of the distal end of the embodiment shown in FIG. 5.

The embodiment shown in FIGS. 5 through 7 has components, which are provided with the same reference numerals as corresponding components shown in the other Figures. This tissue punch accordingly also has a rigid inner shaft curved at its distal end, and an outer shaft 4, which is deformable at least in the area where it must follow the curve of the inner shaft during axial movements.

The previously designated counter cutting edge of the outer shaft 4 and the cutting edge of the inner shaft 3 are in this case rims of holes 27, 28, which for free access to the opening 2 (see FIG. 5) can be brought into alignment, namely through corresponding relative movement of both shafts.

The hole 27 of the outer shaft 4 is located in an elastically bendable cutting part 29, which is a distal continuation of the outer shaft and according to the embodiment in FIG. 5 is movable on a curved course, namely by axial movement of the outer shaft relative to the inner shaft, in order to allow the cutting rims of the holes 27, 28 to shear and to separate the tissue extending through the opening 2 into the inner shaft.

The course of movement of the cutting part 29 is directed by the neighboring contour of the inner shaft 3 and guides 30 at its distal end, whereby the guides grip laterally over the cutting part 29 and hold it in overlying position with the inner shaft.

Practically, the cutting part shown in FIG. 5 is obviously so shaped that during actuation of the tissue punch comparatively little elastic strain or, mechanical stress is placed on the cutting part. This solution also has the advantage that the opening 2 does not have to be laterally directed, as shown in FIG. 1, but can also be directed distally or at least with distal components.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A tissue punch for surgically cutting tissue, comprising an outer shaft (4) overlying an inner shaft (3), said outer and inner shafts having respective proximal and distal ends, said inner shaft (3) having an opening (2) with a first cutting edge (5) at a distal end region thereof, said outer shaft (4) having a second cutting edge (6) which is located at a distal end region thereof and which faces and collaborates with said first cutting edge (5), actuation means for causing relative axial movement between said inner and outer shafts, whereby during operation of said actuation means tissue which extends through the said opening (2) into the inner shaft (3) is separated by said first and second cutting edges (5, 6) moving against each other, said inner shaft being rigid, being straight in a proximal region thereof, and being axially curved in a distal region thereof, and said outer shaft (4) being flexible at least in the curved region of the inner shaft said outer shaft (4) having opposing laterally opening recesses (19, 20) in opposing faces thereof, said opposing recesses lying along radiuses of the curved region of the inner shaft, said inner shaft (3) having an axial inner bore which forms a free lumen (7) connected with the opening (2), and further comprising a connection nozzle (9) having an axial inner bore and being connected to the proximal end of the inner shaft (3), whereby the free lumen (7) is in alignment with the axial inner bore of the connection nozzle (9).

2. A tissue punch according to claim 1, wherein the opening (2) faces laterally of the inner shaft (3) and a proximally directed portion of the opening comprises said first cutting edge (5), and the second cutting edge (6) forms the distal end of the outer shaft (4).

3. A tissue punch according to claim 1, wherein said outer shaft (4) has an elastically deformable cutting part (29), in which the second-cutting edge (6) is located and which is a continuation of the distal end of the outer shaft (4), and the distal end of the inner shaft (3) has guides (30) through which said cutting part (29) is axially movable along a portion of the curved region of the inner shaft.

4. A tissue punch according to claim 3, wherein the cutting edges in both shafts (3, 4) comprise rims of holes (28, 27), said holes being alignable with each other in overlying relationship.

5. A tissue punch according to claim 4 wherein the hole (27) in the outer shaft (4) is located in the cutting part (29).

6. A tissue punch according to claim 4 wherein the hole (28) in the inner shaft (3) is located at the distal end thereof.

7. A tissue punch according to the claim 1, wherein said actuation means comprises a handle part (8) located at proximal end regions of the outer shaft (4) and the inner shaft (3), said handle part (8) comprising scissor legs (13, 13a), one of which is respectively attached to each of the outer shaft (4) and the inner shaft (3) to cause relative axial movement between said shafts.

8. A tissue punch according to claim 7, further comprising a pressure spring (17) attached to the scissor legs (13, 13a), said pressure spring in its non-compressed state holding the inner shaft (3) in relationship to the outer shaft (4) in such a position that the opening (2) of the inner shaft (3) extends distally completely out of the outer shaft (4).

9. A tissue punch according to claim 1, further comprising a motor (21) coupled to one of the shafts (3, 4) for causing oscillating movements of said one shaft relative to the other shaft (4, 3).

10. A tissue punch according to claim 9, wherein the motor (21) is mounted in a housing (22) which forms a handle for the punch.

* * * * *